US008685377B2

(12) United States Patent
Kaftan et al.

(10) Patent No.: US 8,685,377 B2
(45) Date of Patent: *Apr. 1, 2014

(54) AGENT FOR FIBERS CONTAINING KERATIN, COMPRISING AT LEAST ONE SPECIFIC AMPHIPHILIC CATIONIC POLYMER AND AT LEAST ONE SPECIFIC, ADDITIONAL FILM-FORMING ANIONIC AND/OR STABILIZING ANIONIC POLYMER

(75) Inventors: Pamela Kaftan, Hamburg (DE); Burkhard Mueller, Hamburg (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/030,628

(22) Filed: Feb. 18, 2011

(65) Prior Publication Data

US 2011/0142781 A1 Jun. 16, 2011

Related U.S. Application Data

(63) Continuation of application No. PCT/EP2009/059349, filed on Jul. 21, 2009.

(30) Foreign Application Priority Data

Aug. 18, 2008 (DE) .......................... 10 2008 038 106

(51) Int. Cl.
| | | |
|---|---|---|
| *A61K 8/00* | (2006.01) | |
| *A61K 8/18* | (2006.01) | |
| *A61Q 5/00* | (2006.01) | |
| *A61Q 9/00* | (2006.01) | |
| *A61Q 5/12* | (2006.01) | |

(52) U.S. Cl.
USPC ..................................... 424/70.19; 424/70.27

(58) Field of Classification Search
USPC ................ 424/70.11, 70.19, 70.1, 70.27
See application file for complete search history.

(56) References Cited

U.S. PATENT DOCUMENTS

| | | |
|---|---|---|
| 3,753,968 A | 8/1973 | Ward |
| 6,235,913 B1 | 5/2001 | Raths et al. |
| 6,852,815 B1 | 2/2005 | Chuang et al. |
| 7,332,466 B2 | 2/2008 | Schmid et al. |
| 2004/0136921 A1 | 7/2004 | Schulz et al. |
| 2005/0255067 A1 | 11/2005 | Leighton et al. |
| 2006/0013785 A1* | 1/2006 | Lauscher et al. ............. 424/70.9 |
| 2008/0020004 A1 | 1/2008 | Birkel et al. |
| 2010/0028272 A1 | 2/2010 | Knappe et al. |

FOREIGN PATENT DOCUMENTS

| | | |
|---|---|---|
| AU | 730455 B2 | 5/2000 |
| DE | 3139438 A1 | 4/1983 |
| DE | 19756454 C1 | 6/1999 |
| DE | 10240757 A1 | 7/2003 |
| DE | 102007008089 A1 | 8/2008 |

OTHER PUBLICATIONS

Rigoletto et al. Cosmetic Science Technology, 2007, 142-156 (1st page in IDS submitted May 27, 2011).*
Rigoletto, Raymond et al. "Polyquatemium-69: A New Fixative Polymer with Enhanced Styling Benefits." Cosmetic Science Technology, Jan. 1, 2007, p. 142.
"Aquastyle 300." ISP Corporation, Dec. 6, 2006, Retrieved from http://www.ispjapan.co.jp/pc_refguide/pdf/AquaStyle_300_jp, pp. 71, 83-93, on Dec. 3, 2009.
International Cosmetic Ingredient Dictionary & Handbook. The Cosmetic Toiletry and Fragrance Association, 7th Edition, 1997.

* cited by examiner

*Primary Examiner* — Gina C Justice
*Assistant Examiner* — Genevieve S Alley
(74) *Attorney, Agent, or Firm* — Ingrassia Fisher & Lorenz, P.C.

(57) ABSTRACT

Agent for treating fibers containing keratin, particularly human hair, having in a cosmetically acceptable carrier, (a) at least one amphiphilic, cationic polymer comprising at least one structural unit of formulae (I) to (IV), wherein $R^1$ and $R^4$ independently=H or methyl; $X^1$ and $X^2$ independently=O or NH, $A^1$ and $A^2$ independently=ethan-1,2-diyl, propan-1,3-diyl or butan-1,4-diyl, $R^2$, $R^3$, $R^5$ and $R^6$ independently=($C_1$-$C_4$) alkyl, $R^7$=($C_8$-$C_{30}$) alkyl, and (b) at least one film-forming anionic and/or stabilizing anionic polymer comprising at least one structural unit of formula (V) and at least one structural unit of formula (VI), wherein $R^8$ and $R^9$ independently=hydrogen or methyl, with the proviso that $R^8$ and $R^9$ are not simultaneously methyl, $R^{10}$=hydrogen or methyl, $R^{11}$=carbamoyl, linear or branched ($C_4$ to $C_{12}$) alkylaminocarbonyl, linear or branched ($C_4$ to $C_{12}$) alkylaminoethyl-aminocarbonyl, linear or branched ($C_4$ to $C_{12}$) alkylaminopropyl-aminocarbonyl, linear or branched ($C_4$ to $C_{12}$) alkyloxycarbonyl, linear or branched ($C_4$ to $C_{12}$) alkylaminoethyloxycarbonyl, linear or branched ($C_4$ to $C_{12}$) alkylaminopropyloxycarbonyl, linear or branched ($C_2$ to $C_{12}$) acyloxy, $A^3$=hydroxyl or an organic group having at least one sulfonic acid group that bonds through an oxygen atom or an NH group to the structural fragment. The invention also relates to use of agents for temporarily styling hair and for haircare, particularly as aerosol hairspray or aerosol hair mousse.

15 Claims, No Drawings

AGENT FOR FIBERS CONTAINING KERATIN, COMPRISING AT LEAST ONE SPECIFIC AMPHIPHILIC CATIONIC POLYMER AND AT LEAST ONE SPECIFIC, ADDITIONAL FILM-FORMING ANIONIC AND/OR STABILIZING ANIONIC POLYMER

CROSS REFERENCE TO RELATED APPLICATIONS

The present application is a continuation of International Patent Application No. PCT/EP2009/059349 filed 21 Jul. 2009, which claims priority to German Patent Application No. 10 2008 038 106.3 filed 18 Aug. 2008, both of which are incorporated herein by reference.

The present invention relates to agents for treating hair comprising a combination of at least one specific amphiphilic, cationic polymer with at least one specific film-forming anionic and/or setting anionic polymer, use of these agents for the temporary shaping and/or care of keratin-containing fibers, and aerosol hair sprays/foams based on these agents.

Keratin-containing fibers include all animal hair (e.g., wool, horsehair, angora hair, furs, feathers and products or fabrics produced from them). However, keratinic fibers preferably concern human hair.

Today, a suitably looking hairstyle is generally regarded as an essential part of a well groomed appearance. Based on fashion trends, time and again hairstyles are considered chic which, for many types of hair, can only be formed or sustained over a period of up to several days by use of certain consolidating materials. Thus, hair treatments which provide a permanent or temporary hairstyling play an important role. Temporary styling intended to provide a good hold without compromising the healthy appearance of hair, such as gloss, can be obtained, for example, by use of hairsprays, hair waxes, hair gels, hair foams, setting lotions, etc.

Suitable compositions for temporary hairstyling usually contain synthetic polymers as the styling component. Preparations comprising a dissolved or dispersed polymer can be applied onto the hair by propellants or pumping mechanism. Hair gels and hair waxes, however, are generally not applied directly on the hair, but rather dispersed with a comb or by hand.

An important property of an agent for temporary styling of keratin fibers, also referred to as styling agents, involves giving the treated fibers the strongest possible hold for the shape created. If the keratinic fibers are human hair, then one also speaks of a strong hairstyle hold or high degree of hold of the styling agent. Styling hold is determined by the type and quantity of synthetic polymer used; however, other components of the styling agent may also influence hold.

In addition to a high degree of hold, styling agents must fulfill a whole series of additional requirements. These requirements can be broadly divided into hair properties, formulation properties (e.g., properties of the foam, gel or aerosol spray), and properties regarding the handling of the styling agent, with particular importance attached to the properties on the hair. These include moisture resistance, low stickiness and a balanced conditioning effect. Furthermore, a styling agent should be universally applicable for as many types of hair as possible.

In an attempt to meet the various requirements, various synthetic polymers have been developed and are being used in styling agents. These polymers can be divided into cationic, anionic, non-ionic and amphoteric film-forming and/or setting polymers. Ideally, these polymers form a polymer film when applied to hair, imparting a strong hold to the hairstyle while also being sufficiently flexible so as to not to break under stress. If the polymer film is too brittle, film plaques develop (i.e., residues that are shed with movement of the hair and give the impression that the user of the respective styling agent has dandruff).

Developing styling agents that in combination have all the desired properties still presents problems. This is particularly true for the combination of strong hold and simple, uniform application onto the keratin-containing fibers.

Accordingly, the present invention provides an agent for temporary shaping and/or care of keratinic fibers giving a high degree of hold or high care action, wherein the agent particularly has excellent handleability during application onto the keratin-containing fibers.

It has now been surprisingly found that this can be achieved by a combination of specific polymers. Furthermore, it is possible, in addition to these excellent properties, to provide compositions exempt from turbidity. Freedom from turbidity is of particular interest for aerosol compositions, as solid suspended particles can lead to blockage of the discharge nozzle of the aerosol pack. Generally, for turbid and low viscosity compositions there is the additional danger of sedimentation that has a deleterious effect on storage stability of the composition.

Accordingly, a first subject matter of the present invention is an agent for treating keratin-containing fibers, especially human hair, comprising in a cosmetically acceptable carrier (a) at least one amphiphilic, cationic polymer having at least one structural unit of Formula (I), at least one structural unit of Formula (II), at least one structural unit of Formula (III), and at least one structural unit of Formula (IV),

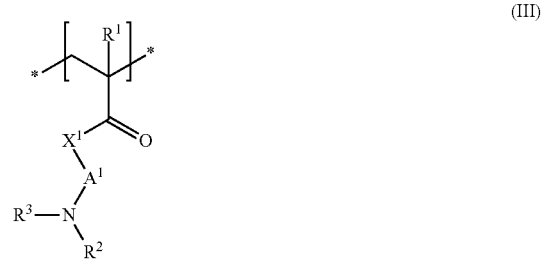

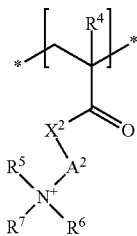

(IV)

wherein
$R^1$ and $R^4$ are, independently of one another, a hydrogen atom or a methyl group,
$X^1$ and $X^2$ are, independently of one another, an oxygen atom or an NH group,
$A^1$ and $A^2$ are, independently of one another, an ethane-1,2-diyl, propane-1,3-diyl or butane-1,4-diyl group,
$R^2$, $R^3$, $R^5$ and $R^6$ are, independently of one another, a ($C_1$ to $C_4$) alkyl group, and
$R^7$ is a ($C_8$ to $C_{30}$) alkyl group, and
(b) at least one film-forming anionic and/or setting anionic polymer having at least one structural unit of Formula (V) and at least one structural unit of Formula (VI),

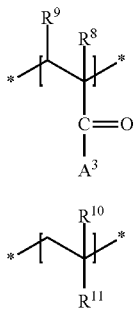

(V)

(VI)

wherein
$R^8$ and $R^9$ are, independently of one another, a hydrogen atom or a methyl group, with the proviso that $R^8$ and $R^9$ are not simultaneously a methyl group,
$R^{10}$ is a hydrogen atom or a methyl group,
$R^{11}$ is a carbamoyl group, a linear or branched ($C_4$ to $C_{12}$) alkylaminocarbonyl group, a linear or branched ($C_4$ to $C_{12}$) alkylaminoethyl-aminocarbonyl group, a linear or branched ($C_4$ to $C_{12}$) alkylaminopropyl-aminocarbonyl group, a linear or branched ($C_4$ to $C_{12}$) alkyloxycarbonyl group, a linear or branched ($C_4$ to $C_{12}$) alkylaminoethyloxycarbonyl group, a linear or branched ($C_4$ to $C_{12}$) alkylaminopropyloxycarbonyl group, a linear or branched ($C_2$ to $C_{12}$) acyloxy group,
$A^3$ is a hydroxyl group or organic group having at least one sulfonic acid group that bonds through an oxygen atom or an NH group to the structural fragment.

Film-forming polymers refer to those polymers that, on drying, leave a continuous film on the skin, the hair or the nails. These types of film former can be used in a wide variety of cosmetic products such as make up masks, make up, hair sets, hair sprays, hair gels, hair waxes, hair conditioners, shampoos or nail varnishes. Those products are particularly preferred that are sufficiently soluble in alcohol or water/alcohol mixtures, so that they are present in completely dissolved form in the agents. The film-forming polymers can be of synthetic or of natural origin.

According to the invention, film-forming polymers further refer to those polymers that, when used in concentrations of 0.1 to 20 wt. % in aqueous, alcoholic or aqueous alcoholic solution, are able to separate out as a transparent polymer film on the hair.

Setting polymers contribute to the hold and/or creation of hair volume and hair body of the whole hairstyle. These polymers are also film-forming polymers and therefore are generally typical substances for styling hair treatment compositions such as hair sets, hair foams, hair waxes, hair sprays. The film formation can be in completely selected areas and bond only some fibers together.

The curl-retention test is frequently used as a test method for the setting action.

In the above Formulae and all Formulae below, the symbol * represents a chemical bond that is a free valence of the corresponding structural fragment.

To compensate for the positive charge on the polymer in the agent, all possible physiologically acceptable anions can be used, such as chloride, bromide, hydrogen sulfate, methyl sulfate, ethyl sulfate, tetrafluoroborate, phosphate, hydrogen phosphate, dihydrogen phosphate or p-toluene sulfonate, or triflate.

Examples of ($C_1$ to $C_4$) alkyl groups are methyl, ethyl, propyl, isopropyl, butyl, sec-butyl, isobutyl, tert-butyl. Exemplary inventive ($C_8$ to $C_{30}$) alkyl groups are octyl (capryl), decyl (caprinyl), dodecyl (lauryl), tetradecyl (myristyl), hexadecyl (cetyl), octadecyl (stearyl), eicosyl (arachyl), docosyl (behenyl).

Examples of ($C_4$ to $C_{12}$) alkylaminocarbonyl groups are butylaminocarbonyl, sec-butylaminocarbonyl, isobutylaminocarbonyl, tert-butylaminocarbonyl, (2,4,4-trimethylpent-2-yl)aminocarbonyl, neopentylaminocarbonyl, 2-ethylhexylaminocarbonyl, neodecylaminocarbonyl.

Examples of ($C_4$ to $C_{12}$) alkylaminoethylaminocarbonyl groups are butylaminoethyl-aminocarbonyl, sec-butylaminoethylaminocarbonyl, isobutylaminoethylaminocarbonyl, tert-butylaminoethylaminocarbonyl, (2,4,4-trimethylpent-2-yl)aminoethylaminocarbonyl, neopentyl-aminoethylaminocarbonyl, 2-ethylhexylaminoethylaminocarbonyl, neodecylaminoethylaminocarbonyl.

Examples of ($C_4$ to $C_{12}$) alkylaminopropylaminocarbonyl groups are butylaminopropylaminocarbonyl, sec-butylaminopropylaminocarbonyl, isobutylaminopropylaminocarbonyl, tert-butylaminopropylaminocarbonyl, (2,4,4-trimethylpent-2-yl)aminopropylaminocarbonyl, neopentylaminopropylaminocarbonyl, 2-ethylhexylaminopropylaminocarbonyl, neodecylaminopropylaminocarbonyl.

Examples of ($C_4$ to $C_{12}$) alkyloxycarbonyl groups are butyloxycarbonyl, sec-butyloxycarbonyl, isobutyloxycarbonyl, tert-butyloxycarbonyl, (2,4,4-trimethylpent-2-yl)oxycarbonyl, neopentyloxycarbonyl, 2-ethylhexyloxycarbonyl, neodecyloxycarbonyl.

Examples of ($C_4$ to $C_{12}$) alkylaminoethyloxycarbonyl groups are butylaminoethyloxycarbonyl, sec-butylaminoethyloxycarbonyl, isobutylaminoethyloxycarbonyl, tert-butylaminoethyloxycarbonyl, (2,4,4-trimethylpent-2-yl)aminoethyloxycarbonyl, neopentylaminoethyloxycarbonyl, 2-ethylhexylaminoethyloxycarbonyl, neodecylaminoethyloxycarbonyl.

Examples of ($C_4$ to $C_{12}$) alkylaminopropyloxycarbonyl groups are butylaminopropyloxycarbonyl, sec-butylaminopropyloxycarbonyl, isobutylaminopropyloxycarbonyl, tert-butylaminopropyloxycarbonyl, (2,4,4-trimethylpent-2-yl)aminopropyloxycarbonyl, neopentylaminopropyloxycarbonyl, 2-ethylhexylaminopropyloxycarbonyl, neodecylaminopropyloxycarbonyl.

Examples of ($C_4$ to $C_{12}$) alkyl groups are butyl, sec-butyl, isobutyl, tert-butyl, 2,4,4-trimethylpent-2-yl, neopentyl, 2-ethylhexyl, neodecyl.

Examples of ($C_2$ to $C_{12}$) acyloxy groups are acetoxy, propionyloxy and neodecanoyloxy.

Molecular weights of the amphiphilic, cationic polymers according to the invention are preferably from 10,000 g/mol to 50,000,000 g/mol, especially from 50,000 g/mol to 5,000,000 g/mol, particularly preferably from 75,000 g/mol to 1,000,000 g/mol.

According to the invention, preferred agents contain amphiphilic, cationic polymers (a) in an amount of 0.1 wt. % to 20.0 wt. %, preferably 0.2 wt. % to 10.0 wt. %, more preferably 0.5 wt. % to 5.0 wt. %, based on total weight of the agent.

Properties of the agent have proven to be particularly advantageous when the agent is packaged as an aerosol spray, aerosol foam, pump spray or pump foam. This preferred packaging form is described later in detail.

The following amphiphilic, cationic polymers (a) are preferably used in the agents when the amphiphilic, cationic polymers (a) corresponding to the above Formulas (I) to (IV) fulfill one or more of the following criteria:

$R^1$ and $R^4$ are each a methyl group, $X^1$ is an NH group, $X^2$ is an NH group, $A^1$ and $A^2$ are, independently of one another, ethane-1,2-diyl or propane-1,3-diyl, $R^2$, $R^3$, $R^5$ and $R^6$ are, independently of one another, methyl or ethyl, (preferably methyl), and $R^7$ is a ($C_{10}$ to $C_{24}$) alkyl group, especially decyl (caprinyl), dodecyl (lauryl), tetradecyl (myristyl), hexadecyl (cetyl), octadecyl (stearyl), eicosyl (arachyl) or docosyl (behenyl).

Preferably, the structural unit of Formula (III) is chosen from at least one of the structural units of Formulae (III-1) to (III-8)

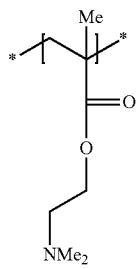
(III-1)

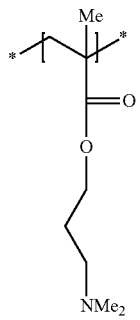
(III-2)

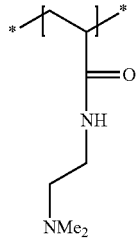
(III-3)

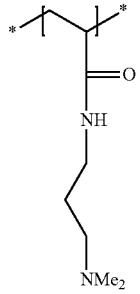
(III-4)

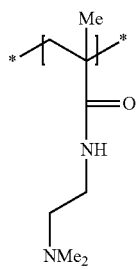
(III-5)

(III-6)

(III-7)

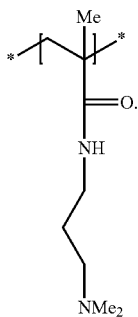
(III-8)

Moreover, it is particularly preferable to choose the structural unit according to Formula (III-7) and/or of Formula (III-8) as the structural unit from Formula (III). According to the invention, the structural unit of Formula (III-8) is a quite particularly preferred structural unit.

Furthermore, the structural unit of Formula (IV) is preferably chosen from at least one structural unit of Formulae (IV-1) to (IV-8)

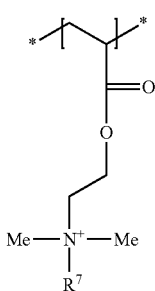
(IV-1)

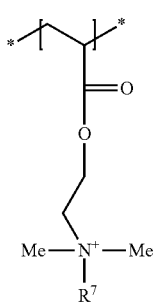
(IV-2)

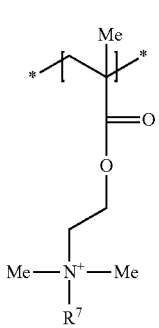
(IV-3)

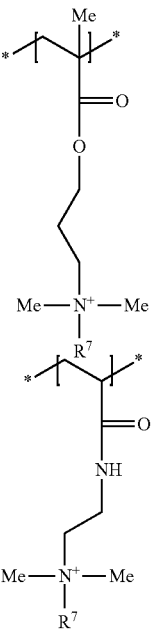
(IV-4)

(IV-5)

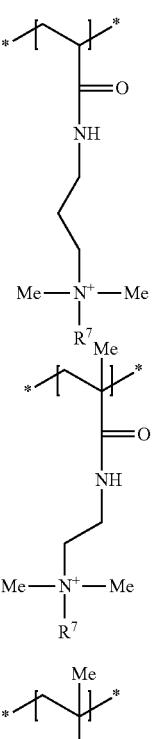
(IV-6)

(IV-7)

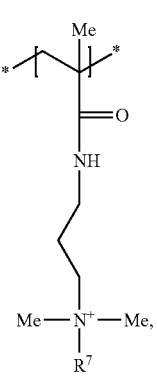
(VI-8)

wherein each $R^7$ is a ($C_8$ to $C_{30}$) alkyl group.

The structural units of Formula (IV-7) and/or of Formula (IV-8) are particularly preferred as the structural unit of Formula (IV), wherein each $R^7$ is octyl (capryl), decyl (caprinyl), dodecyl (lauryl), tetradecyl (myristyl), hexadecyl (cetyl), octadecyl (stearyl), eicosyl (arachyl), or docosyl (behenyl). According to the invention, the structural unit of Formula (IV-8) represents a quite particularly preferred structural unit of Formula (IV).

An amphiphilic, cationic polymer having at least one structural unit of Formula (II), at least one structural unit of Formula (III-8), and at least one structural unit of Formula (IV-8) is quite preferably present in the agent according to the invention

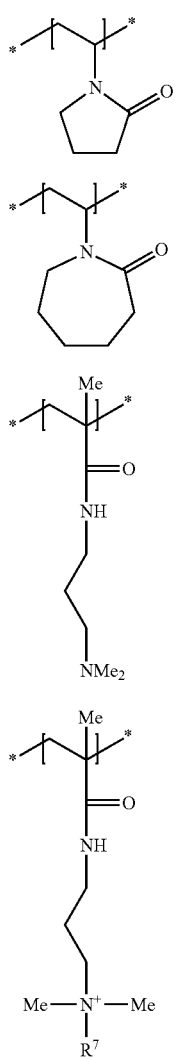

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl).

A particularly preferred amphiphilic, cationic polymer according to the invention is the copolymer of N-vinyl pyrrolidone, N-vinyl caprolactam, N-(3-dimethylaminopropyl) methacrylamide and 3-(methacryloylamino)propyl-lauryl-dimethylammonium chloride (INCI name: Polyquaternium-69), marketed, for example, under the trade name AquaStyle® 300 (28-32 wt. % active substance in an ethanol-water mixture, molecular weight 350 000) by the ISP company.

Additionally, agents according to the invention contain at least one anionic, film-forming and/or anionic, setting polymer (b). An anionic polymer refers to a polymer that, in a protic solvent under standard conditions, has structural units containing anionic groups that have to be compensated by counter ions in order to maintain electro neutrality and that does not have any structural units containing permanently cationic groups. Anionic groups include carboxylic and sulfonic acid groups.

The agent preferably includes anionic, film-forming and/or anionic, setting polymers (b) in an amount of 0.1 wt. % to 20.0 wt. %, more preferably 0.2 wt. % to 15.0 wt. %, quite preferably 0.5 wt. % to 10.0 wt. %, based on total weight of the agent.

Preferably, the film-forming anionic and/or setting anionic polymer (b) has at least one structural unit of Formula (V) chosen from at least one structural unit of Formulae (V-1) to (V-5)

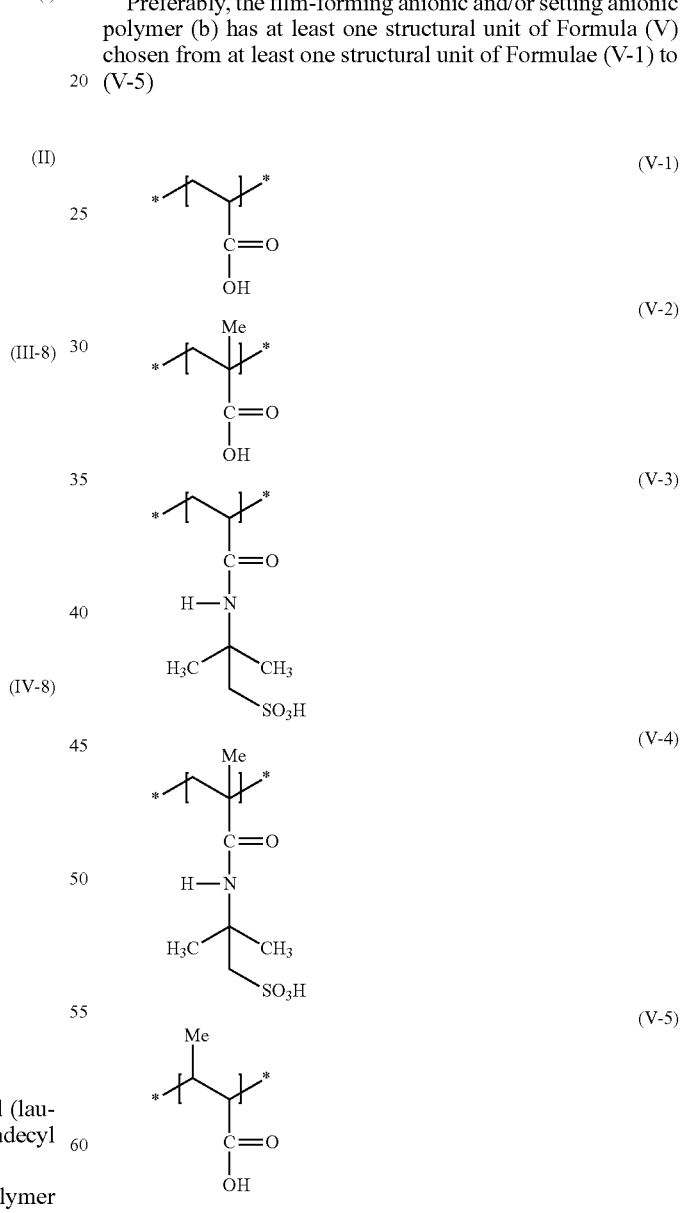

Here, it is particularly preferred when polymer (b) additionally has, in addition to the above structural units of Formulae (V) and (VI), at least one structural unit of Formula (VII)

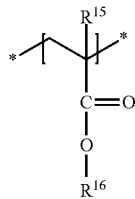

(VII)

wherein

R¹⁵ is a hydrogen atom or a methyl group, and

R¹⁶ is a ($C_1$ to $C_4$) alkyl group (particularly a methyl or ethyl group).

Copolymers of methacrylic acid and ethyl acrylate and tert-butyl acrylate, for example, are preferred.

Preferably, the film-forming anionic and/or setting anionic polymer (b) has at least one structural unit of Formula (VI) chosen from at least one structural unit of Formulae (VI-1) to (VI-15)

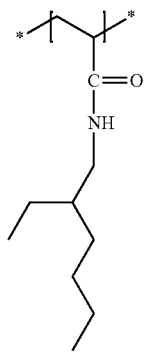

(VI-1)

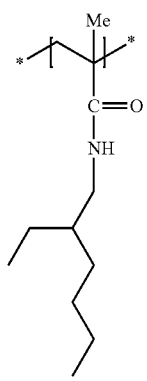

(VI-2)

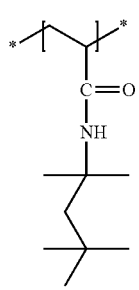

(VI-3)

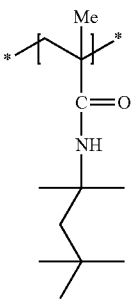

(VI-4)

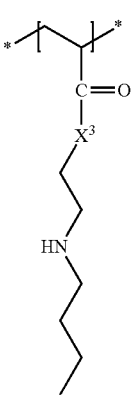

(VI-5)

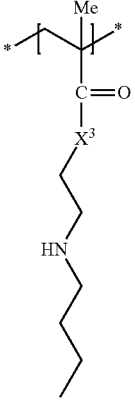

(VI-6)

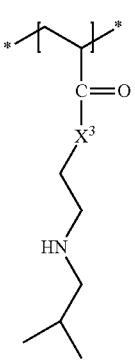

(VI-7)

(VI-8)
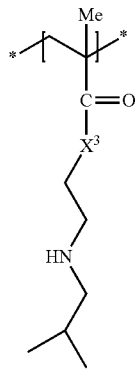

(VI-9)
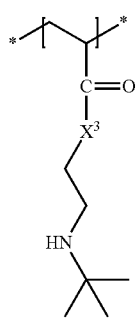

(VI-10)
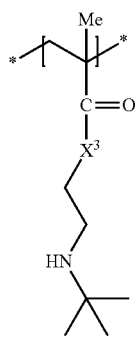

(VI-11)
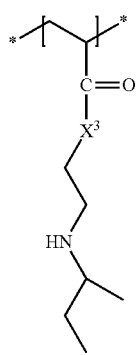

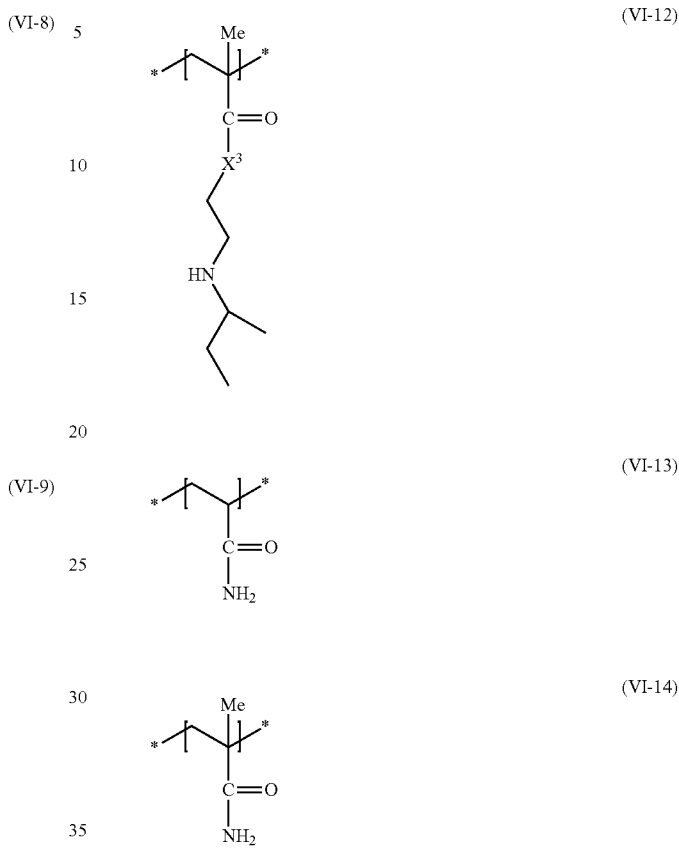

wherein
$X^3$ is an oxygen atom or an NH group, and
$R^{12}$ is a ($C_2$ to $C_{12}$) acyl group (especially acetyl or neodecanoyl).

Preferably, $X^3$ in Formulae (VI-5) to (VI-12) is an oxygen atom.

According to a first preferred embodiment of the invention, the agent has at least one film-forming anionic and/or setting anionic polymer (b) containing at least one structural unit of Formula (V-1), at least one structural unit of Formula (VI-3), and at least one structural unit of Formula (VI-16) (particularly chosen from the above Formulae (VI-5) to (VI-12) with the proviso that $X^3$ is an oxygen atom),

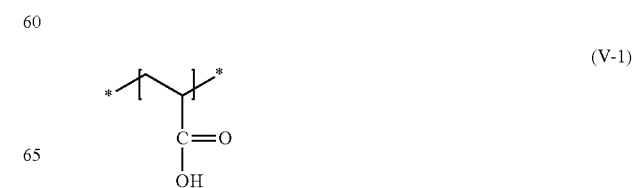

-continued

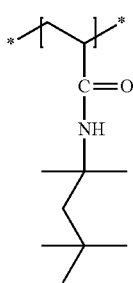
(VI-3)

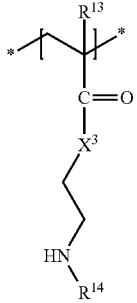
(VI-16)

wherein
$X^3$ is an oxygen atom or an NH group,
$R^{13}$ is a hydrogen atom or methyl group, and
$R^{14}$ is an alkyl group containing 4 carbon atoms (particularly n-butyl, sec-butyl, iso-butyl or tert-butyl).

Preferably, polymer (b) also has, in addition to the structural units of Formula (V-1), (VI-3) and (VI-16), at least one structural unit of Formula (VII)

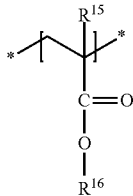
(VII)

wherein
$R^{15}$ is a hydrogen atom or a methyl group
$R^{16}$ is a ($C_1$ to $C_4$) alkyl group (particularly a methyl or ethyl group).

Preferred polymers (b) of this type are chosen from: copolymers of acrylic acid, ($C_1$ to $C_4$) alkyl acrylates, $C_4$ alkylaminoethyl methacrylate and $C_8$ alkyl acrylamide.

An example of a polymer (b) that is particularly preferably used is the polymer with the INCI name Octylacrylamide/Acrylates/Butylaminoethylmethacrylate Copolymer, available under the trade name Amphomer® 028-4910 from the National Starch Company.

Accordingly, those particular agents are quite particularly preferred that have, in a cosmetically acceptable carrier (a) at least one amphiphilic, cationic polymer having at least one structural unit of Formula (I), at least one structural unit of Formula (II), at least one structural unit of Formula (III-8) and at least one structural unit of Formula (IV-8)

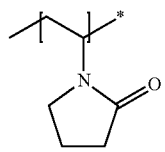
(I)

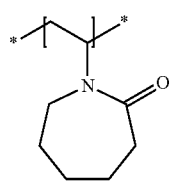
(II)

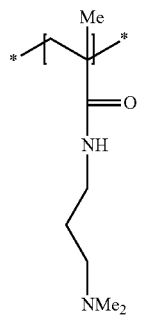
(III-8)

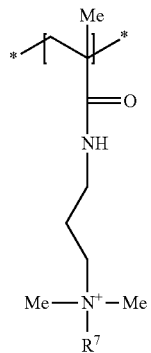
(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one anionic film-forming and/or anionic setting polymer (b) having at least one structural unit of Formula (V-1), at least one structural unit of Formula (VI-3) and at least one structural unit of Formula (VI-16),

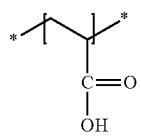
(V-1)

-continued

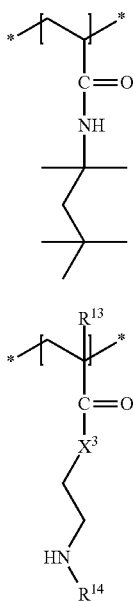

(VI-3)

(VI-16)

wherein
$X^3$ is an oxygen atom or an NH group (especially an oxygen atom),
$R^{13}$ is a hydrogen atom or a methyl group (especially a methyl group), and
$R^{14}$ is an alkyl group containing 4 carbon atoms (particularly n-butyl, sec-butyl, iso-butyl or tert-butyl).

Preferably, polymer (b) also contains, in addition to structural units of Formulae (V-1), (VI-3) and (VI-16), at least one structural unit of Formula (VII)

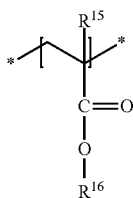

(VII)

wherein
$R^{15}$ is a hydrogen atom or a methyl group
$R^{16}$ is a ($C_1$ to $C_4$) alkyl group (particularly a methyl or ethyl group).

Here, it is particularly preferred when the structural unit of Formula (V-1) is totally or partially neutralized. At least one alkanolamine is preferably used for neutralization. The alkanolamines that can be used as the inventive alkalization agent are preferably chosen from primary amines containing a $C_2$-$C_6$ alkyl parent substance having at least one hydroxyl group. Particularly preferred alkanolamines are chosen from 2-aminoethane-1-ol (monoethanolamine), 3-aminopropane-1-ol, 4-aminobutane-1-ol, 5-aminopentane-1-ol, 1-amino-propane-2-ol, 1-aminobutane-2-ol, 1-aminopentane-2-ol, 1-aminopentane-3-ol, 1-aminopentane-4-ol, 3-amino-2-methylpropane-1-ol, 1-amino-2-methylpropane-2-ol, 3-amino-propane-1,2-diol, and 2-amino-2-methylpropane-1,3-diol. Quite particularly preferred alkanolamines are chosen from 2-aminoethane-1-ol, 2-amino-2-methylpropane-1-ol and 2-amino-2-methyl-propane-1,3-diol.

According to a second embodiment, those agents are preferred that have as the anionic film-forming and/or anionic setting polymer (b) at least one polymer having at least one structural unit of Formula (V-3) and at least one structural unit of Formula (V-13)

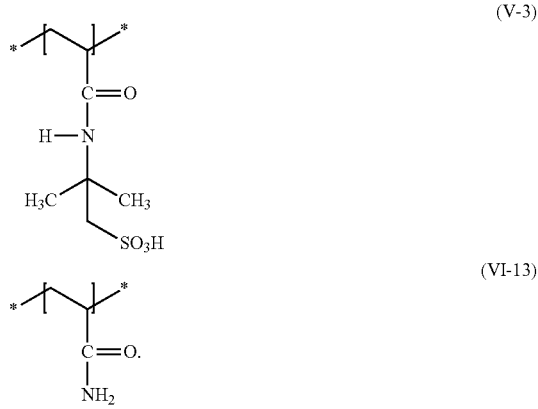

(V-3)

(VI-13)

Preferred polymers (b) of this type are chosen from at least one polymer from
copolymers of 2-acrylamido-2-methyl-propane sulfonic acid and acrylamide, and/or
copolymers of 2-acrylamido-2-methyl-propane sulfonic acid, acrylamide and acrylic acid.

Polymers of this type are marketed, for example, in an inverse isohexadecane emulsion by Seppic under the trade name Sepigel® 305 (INCI name: Polyacrylamide, C13-14 Isoparaffin, Laureth-7) or Simulgel® 600 (INCI name: Acrylamide/Acryloyldimethyltaurate Copolymer, Isohexadecane, Polysorbate-80).

An particularly preferred agent has a copolymer (bI) as the polymer (b).

These copolymers (bI) can be described by the general Formula

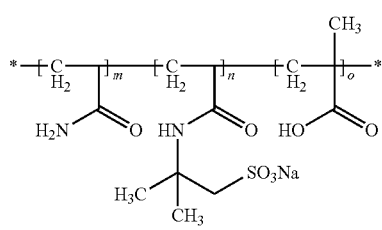

wherein m and n vary according to the molecular mass of the polymer and are not intended to mean to portray block copolymers. In fact, structural units can be statistically distributed in the molecule.

Here, those compositions are particularly preferred wherein the molecular mass of copolymer (bI) is from 50 to 500 kDa, preferably from 100 to 450 kDa, more preferably from 150 to 400 kDa, and particularly from 200 to 300 kDa.

Copolymers of acrylamide with methacrylic acid and acryloyldimethyl taurate are available, for example, under the trade name Acudyne® SCP (Rohm & Haas).

Accordingly, those agents are particularly preferred that have in a cosmetically acceptable carrier
(a) at least one amphiphilic, cationic polymer having at least one structural unit of Formula (II), at least one structural unit of Formula (III-8), and at least one structural unit of Formula (IV-8)

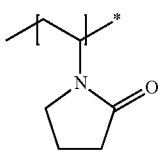
(I)

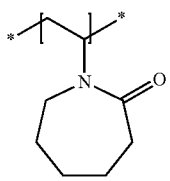
(II)

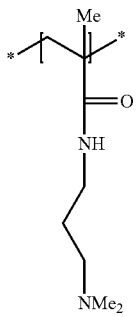
(III-8)

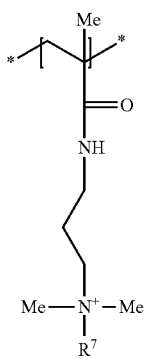
(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one anionic film-forming and/or anionic setting polymer (b) having at least one structural unit of Formula (V-5), and at least one structural unit of Formula (V-13),

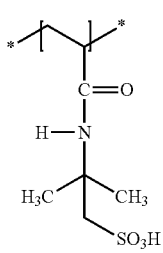
(V-3)

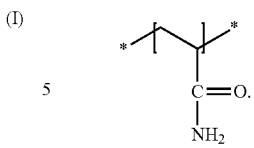
(VI-13)

According to a third embodiment, those agents are preferred that have as the anionic film-forming and/or anionic setting polymer (b) at least one polymer having at least one structural unit of Formula (V-3) and at least one structural unit of Formula (V-13)

(V-5)

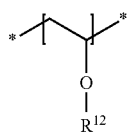
(VI-15)

wherein $R^{12}$ is a ($C_2$ to $C_{12}$) acyl group (especially acetyl or neodecanoyl). Particularly preferred polymers (b) of this type are chosen from at least one polymer from the group of
copolymers of vinyl acetate and crotonic acid,
copolymers of vinyl propionate and crotonic acid, and
copolymers of vinyl neodecanoate, vinyl acetate and crotonic acid.

Copolymers of this type are available, for example, from Clariant under the trade name Aristoflex A 60 (INCI name: VA/Crotonates Copolymer) in an isopropanol-water mixture (60 wt. % active substance), by BASF under the trade name Luviset CA 66 (vinyl acetate/crotonic acid copolymer 90:10, INCI name VA/Crotonates Copolymer, by National Starch under the trade name Resyn 28-2942 or Resyn 28-2930 (INCI name: VA/Crotonates/Vinyl Neodecanoate Copolymer).

Accordingly, those agents are particularly preferred that have in a cosmetically acceptable carrier
(a) at least one amphiphilic, cationic polymer having at least one structural unit of Formula (II), at least one structural unit of Formula (III-8) and at least one structural unit of Formula (IV-8)

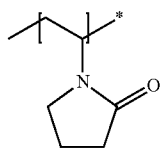
(I)

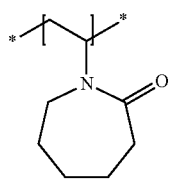
(II)

-continued

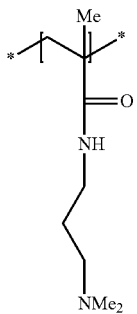
(III-8)

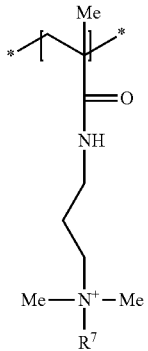
(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl), and (b) at least one anionic film-forming and/or anionic setting polymer (b) having at least one structural unit of Formula (V-5) and at least one structural unit of Formula (V-15)

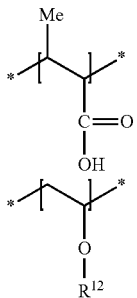
(V-5)

wherein $R^{12}$ is a ($C_2$ to $C_{12}$) acyl group (especially acetyl or neodecanoyl).

According to this embodiment, the previously cited preferred embodiments of the amphiphilic, cationic polymer (a) are preferred (see above). Similarly, all previously mentioned quantitative data regarding polymer components (a) and (b) of the agent are also preferred *mutatis mutandis* for these embodiments.

Here it is particularly preferred when the structural unit of Formula (V-5) in all embodiments of this third embodiment is totally or partially neutralized. At least one alkanolamine is preferably used for neutralization. Alkanolamines that can be used as the alkalization agent are preferably chosen from primary amines containing a $C_2$-$C_6$ alkyl parent substance having at least one hydroxyl group. Particularly preferred alkanolamines are chosen from 2-aminoethane-1-ol (monoethanolamine), 3-aminopropane-1-ol, 4-aminobutane-1-ol, 5-aminopentane-1-ol, 1-aminopropane-2-ol, 1-aminobutane-2-ol, 1-aminopentane-2-ol, 1-aminopentane-3-ol, 1-aminopentane-4-ol, 3-amino-2-methylpropane-1-ol, 1-amino-2-methylpropane-2-ol, 3-aminopropane-1,2-diol, 2-amino-2-methylpropane-1,3-diol. Quite particularly preferred alkanolamines are chosen from 2-aminoethane-1-ol, 2-amino-2-methylpropane-1-ol and 2-amino-2-methyl-propane-1,3-diol.

In order to intensify the effect, the agents preferably also have at least one surfactant, wherein non-ionic, anionic, cationic, ampholytic surfactants are suitable. Ampholytic or amphoteric surfactants includes zwitterionic surfactants and ampholytes. According to the invention, the surfactants can already have an emulsifying action.

Agents according to the invention preferably contain additional surfactants in an amount of 0.01 wt. % to 5 wt. %, more preferably 0.05 wt. % to 0.5 wt. %, based on total weight of the agent.

Preferably, the agents have at least one non-ionic surfactant.

Non-ionic surfactants have, for example, a polyol group, a polyalkylene glycol ether group, or a combination of polyol ether and polyglycol ether groups as the hydrophilic group. Examples of compounds of this type are addition products of 2 to 100 moles ethylene oxide and/or 1 to 5 moles propylene oxide to linear and branched fatty alcohols containing 8 to 30 carbon atoms, to fatty acids containing 8 to 30 carbon atoms and to alkyl phenols containing 8 to 15 carbon atoms in the alkyl group, methyl or $C_2$-$C_6$ alkyl group end blocked addition products of 2 to 50 moles ethylene oxide and/or 1 to 5 moles propylene oxide to linear and branched fatty alcohols with 8 to 30 carbon atoms, to fatty acids with 8 to 30 carbon atoms and to alkyl phenols with 8 to 15 carbon atoms in the alkyl group, such as, for example, the commercially available types Dehydrol® LS, Dehydrol® LT (Cognis), $C_{12}$-$C_{30}$ fatty acid mono- and diesters of addition products of 1 to 30 moles ethylene oxide to glycerin, addition products of 5 to 60 moles ethylene oxide on castor oil and hydrogenated castor oil, polyol esters of fatty acids, such as the commercial product Hydagen® HSP (Cognis) or Sovermol types (Cognis), alkoxylated triglycerides, alkoxylated alkyl esters of fatty acids of Formula (E4-I), $$R^1CO—(OCH_2CHR^2)_wOR^3 \qquad (E4\text{-}I)$$

wherein $R^1CO$ is a linear or branched, saturated and/or unsaturated acyl group with 6 to 22 carbon atoms, $R^2$ is hydrogen or methyl, $R^3$ is linear or branched alkyl groups with 1 to 4 carbon atoms, and w is a number from 1 to 20, amine oxides, mixed hydroxy ethers, such as are described in DE-OS 1 973 8866, sorbitol esters of fatty acids and addition products of ethylene oxide to sorbitol esters of fatty acids such as the polysorbates, sugar esters of fatty acids and addition products of ethylene oxide to sugar esters of fatty acids, addition products of ethylene oxide to fatty acid alkanolamides and fatty amines, sugar surfactants of the type alkyl and alkenyl oligoglycosides according to Formula (E4-II), $$R^4O\text{-}[G]_p \qquad (E4\text{-}II)$$

wherein $R^4$ is an alkyl or alkenyl group containing 4 to 22 carbon atoms, G is a sugar group containing 5 or 6 carbon atoms, and p is a number from 1 to 10. They can be obtained according to the appropriate methods of preparative organic chemistry.

Alkylene oxide addition products to saturated, linear fatty alcohols and fatty acids, each with 2 to 100 moles ethylene oxide per mole fatty alcohol or fatty acid, are particularly preferred non-ionic surfactants. Similarly, preparations with excellent properties are obtained when they contain $C_{12}$-$C_{30}$ fatty acid mono- and diesters of addition products of 1 to 30 moles ethylene oxide to glycerin and/or addition products of 5 to 60 moles ethylene oxide to castor oil and hydrogenated castor oil as the non-ionic surfactants.

The agents preferably have as the surfactant at least one addition product of 15 to 100 moles ethylene oxide, especially 15 to 50 moles ethylene oxide on a linear or branched (especially linear) fatty alcohol containing 8 to 22 carbon atoms. These are preferably Ceteareth-15, Ceteareth-25 or Ceteareth-50, marketed as Eumulgin® CS 15 (COGNIS), Cremophor A25 (BASF SE) or Eumulgin® CS 50 (COGNIS).

Suitable anionic surfactants include all anionic surface-active materials suitable for use on the human body. They have a water solubilizing anionic group, such as a carboxylate, sulfate, sulfonate or phosphate group, and a lipophilic alkyl group containing about 8 to 30 carbon atoms. In addition, the molecule can have glycol or polyglycol ether groups, ester, ether and amide groups, as well as hydroxyl groups. Examples of suitable anionic surfactants, each in the form of the sodium, potassium and ammonium as well as the mono-, di- and trialkanolammonium salts containing 2 to 4 carbon atoms in the alkanol group, are linear and branched fatty acids with 8 to 30 carbon atoms (soaps),
ether carboxylic acids of the formula R—O—($CH_2$—$CH_2O)_x$—$CH_2$—COOH, wherein R is a linear alkyl group containing 8 to 30 carbon atoms and x=0 or 1 to 16,
acyl sarcosides with 8 to 24 carbon atoms in the acyl group,
acyl taurides with 8 to 24 carbon atoms in the acyl group,
acyl isethionates with 8 to 24 carbon atoms in the acyl group,
mono and dialkyl esters of sulfosuccinic acid containing 8 to 24 carbon atoms in the alkyl group and
sulfosuccinic acid mono alkyl polyoxyethyl esters with 8 to 24 carbon atoms in the alkyl group and 1 to 6 oxyethyl groups,
linear alkane sulfonates containing 8 to 24 carbon atoms,
linear alpha-olefin sulfonates containing 8 to 24 carbon atoms,
alpha-sulfo fatty acid methyl esters of fatty acids containing 8 to 30 carbon atoms,
alkyl sulfates and alkyl polyglycol ether sulfates of formula R—O ($CH_2$—$CH_2O)_x$—$OSO_3H$, wherein R is preferably a linear alkyl group containing 8 to 30 carbon atoms and x=0 or 1 to 12,
mixtures of surface active hydroxyl sulfonates, sulfated hydroxyalkyl polyethylene glycol ethers and/or hydroxyalkylene propylene glycol ethers,
sulfonated unsaturated fatty acids with 8 to 24 carbon atoms and 1 to 6 double bonds,
esters of tartaric acid and citric acid with alcohols, which represent the addition products of about 2-15 molecules of ethylene oxide and/or propylene oxide on fatty alcohols containing 8 to 22 carbon atoms,
sulfated fatty acid alkylene glycol esters of the formula (E1-11)   $R^7CO(AlkO)_nSO_3M$   (E1-11),   wherein $R^7CO$— is a linear or branched, aliphatic, saturated and/or unsaturated acyl group with 6 to 22 carbon atoms, Alk is $CH_2CH_2$, $CHCH_3CH_2$ and/or $CH_2CHCH_3$, n is a number from 0.5 to 5, and M is a cation, as described in DE-OS 197 36 906,
amido ether carboxylic acids,
condensation products of $C_8$-$C_{30}$ fatty alcohols with protein hydrolyzates and/or amino acids and their derivatives, known to one skilled in the art as albumin fatty acid condensates, such as the Lamepon® types, Gluadin® types, Hostapon® KCG or the Amisoft® types.

Preferred anionic surfactants are alkyl sulfates, alkyl polyglycol ether sulfates and ether carboxylic acids with 10 to 18 C atoms in the alkyl group and up to 12 glycol ether groups in the molecule, sulfosuccinic acid mono and dialkyl esters with 8 to 18 C atoms in the alkyl group and sulfosuccinic acid mono-alkyl polyoxyethyl esters with 8 to 18 C atoms in the alkyl group and 1 to 6 oxyethylene groups, monoglycerin disulfates, alkyl and alkenyl ether phosphates as well as albumin fatty acid condensates.

According to the invention, cationic surfactants of the type quaternary ammonium compounds, esterquats and amido amines can likewise be used. Preferred quaternary ammonium compounds are ammonium halides, especially chlorides and bromides, such as alkyl-trimethylammonium chlorides, dialkyldimethylammonium chlorides and trialkylmethylammonium chlorides. Long alkyl chains of these surfactants preferably have 10 to 18 carbon atoms, such as in cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Further preferred cationic surfactants are the imidazolium compounds known under the INCI names Quaternium-27 and Quaternium-83.

Zwitterionic surfactants are surface-active compounds having at least one quaternary ammonium group and at least one —COO(—) or —$SO_3$(—) group in the molecule. Particularly preferred suitable zwitterionic surfactants are betaines such as N-alkyl-N,N-dimethylammonium glycinates, for example, cocoalkyl-dimethylammonium glycinate, N-acyl-aminopropyl-N,N-dimethylammonium glycinate, for example, coco-acylaminopropyl-dimethylammonium glycinate, and 2-alkyl-3-carboxymethyl-3-hydroxyethyl-imidazolines, each with 8 to 18 carbon atoms in the alkyl or acyl group, as well as cocoacyl-aminoethylhydroxyethylcarboxymethyl glycinate. A preferred zwitterionic surfactant is the fatty acid amide derivative known under the INCI name Cocamidopropyl Betaine.

Ampholytes include such surface-active compounds that, apart from a $C_{8-24}$ alkyl or acyl group, have at least one free amino group and at least one —COOH or —$SO_3H$ group in the molecule, and are able to form internal salts. Examples of suitable ampholytes are N-alkylglycines, N-alkyl propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids, each with about 8 to 24 carbon atoms in the alkyl group. Particularly preferred ampholytes are N-cocoalkylamino propionate, cocoacylaminoethylamino propionate and $C_{12}$-$C_{18}$ acyl sarcosine.

Compositions according to the invention contain the polymers in a cosmetically acceptable carrier.

Preferred cosmetically acceptable carriers are aqueous, alcoholic or aqueous alcoholic media having preferably at least 10 wt. % water, based on total composition. In particular, lower alcohols containing 1 to 4 carbon atoms, such as ethanol and isopropanol, which are typically used for cosmetic purposes, can be used as alcohols. Preferably, at least one ($C_1$ to $C_4$) monoalkyl alcohol is incorporated into the agents, particularly in an amount of 1 to 50 wt. %, especially 5 to 30 wt. %. This is particularly preferred when manufacturing pump foams or aerosol foams.

Organic solvents or mixture of solvents with a boiling point of 400° C. or less can be used as additional co-solvents in an amount of 0.1 to 15 wt. %, preferably 1 to 10 wt. %, based on total agent. Particularly useful co-solvents are unbranched or branched hydrocarbons such as pentane, hexane, isopentane, and cyclic hydrocarbons such as cyclopentane and cyclohexane. Additional, preferred water-soluble solvents are glycerin, ethylene glycol and propylene glycol in an amount of up to 30 wt. %, based on total weight of the agent.

The addition of glycerin and/or propylene glycol and/or polyethylene glycol and/or polypropylene glycol increases the flexibility of the polymer film formed when the agent is used. Consequently, if a more flexible hold is desired then the agents preferably contain 0.01 to 30 wt. % glycerin and/or propylene glycol and/or polyethylene glycol and/or polypropylene glycol, based on total weight of the agent.

The agents preferably have a pH of 2 to 11. The pH range is more preferably from 2 to 8. Herein, pH data refers to the pH at 25° C. unless otherwise stated.

Agents according to the invention can also contain auxiliaries and additives typically incorporated into styling agents.

In particular, care products may be mentioned as suitable auxiliaries and additives.

Silicone oil and/or a silicone gum, for example, can be used as the care substance.

Suitable silicone oils or silicone gums include dialkyl and alkylarylsiloxanes, such as dimethylpolysiloxane and methylphenylpolysiloxane, as well as their alkoxylated, quaternized or also anionic derivatives. Cyclic and linear polydialkylsiloxanes, their alkoxylated and/or aminated derivatives, dihydroxypolydimethylsiloxanes and polyphenylalkylsiloxanes are preferred.

Silicone oils provide a variety of effects. Thus, for example, they simultaneously influence dry and wet combability, feel of dry and wet hair, as well as gloss. The term "silicone oils" refers to organosilicon compounds with a plurality of structures. In the first instance they include dimethiconols. The following commercial products are given as examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF—R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzene sulfonate (A & E Cannock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401 DC (all from Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all from Dow Corning Corporation), Dub Gel SI 1400 (Stearinerie Dubois Fils), HVM 4852 Emulsion (Crompton Corporation), Jeesilc 6056 (Jeen International Corporation), Lubrasil, Lubrasil DS (both from Guardian Laboratories), Nonychosine E, Nonychosine V (both from Exsymol), San-Surf Petrolatum-25, Satin Finish (both from Collaborative Laboratories, Inc.), Silatex-D30 (Cosmetic Ingredient Resources), Silsoft 148, Silsoft E-50, Silsoft E-623 (all from Crompton Corporation), SM555, SM2725, SM2765, SM2785 (all from GE Silicones), Taylor T-Sil CD-1, Taylor TME-4050E (all from Taylor Chemical Company), TH V 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all from Wacker-Chemie GmbH).

Dimethicones form the second group of silicones that can be used. They can be linear, branched, cyclic, or cyclic and branched.

Dimethicone copolyols (S3) form a further group of suitable silicones. Suitable Dimethicone copolyols are commercially available and marketed, for example, by Dow Corning under the trade name Dow Corning® 5330 Fluid.

Naturally, the Dimethiconols, Dimethicones and/or Dimethicone copolymers can already be present as an emulsion. Emulsions of Dimethiconols, Dimethicones and/or Dimethicone copolymers can be produced both after production of the corresponding Dimethiconols, Dimethicones and/or Dimethicone copolymers from these and the usual emulsification processes known to one skilled in the art. Cationic, anionic, non-ionic or zwitterionic surfactants and emulsifiers can be used as auxiliaries and adjuvants for production of the corresponding emulsions. Naturally, the emulsions of Dimethiconols, Dimethicones and/or Dimethicone copolymers can also be directly produced by an emulsion polymerization process. These types of processes are also well known to one skilled in the art.

When Dimethiconols, Dimethicones and/or Dimethicone copolymers are used as an emulsion, then droplet size of the emulsified particles ranges from 0.01 to 10,000 µm, preferably 0.01 to 100 µm, more preferably 0.01 to 20 µm, and quite preferably 0.01 to 10 µm. Particle size is determined according to the light scattering method.

If branched Dimethiconols, Dimethicones and/or Dimethicone copolymers are used, then the branching is greater than a fortuitous branching that accidentally occurs from impurities in the respective monomers. Accordingly, the degree of branching is greater than 0.01% for branched Dimethiconols, Dimethicones and/or Dimethicone copolymers. The degree of branching is preferably greater than 0.01%, and quite preferably greater than 0.5%. The degree of branching is determined from the ratio of unbranched monomers to branched monomers (i.e., the amount of tri- and tetrafunctional siloxanes). According to the invention, low-branched and highly branched Dimethiconols, Dimethicones and/or Dimethicone copolymers can be used.

Further suitable silicones are amino-functional silicones, especially silicones compiled under the INCI name Amodimethicone. Consequently, the agents also preferably have at least one amino-functional silicone. These include silicones having at least one, optionally substituted, amino group. These silicones are designated as Amodimethicones according to the INCI nomenclature and are available, for example, in the form of an emulsion as the commercial product Dow Corning® 939 or as the commercial product Dow Corning® 949 in a mixture with a cationic and a non-ionic surfactant.

Preferably, those amino functional silicones are used which have an amine number of 0.25 meq/g or greater, preferably 0.3 meq/g or greater, and more preferably 0.4 meq/g or greater. The amine number is the milli-equivalents of amine per gram of amino functional silicone. It can be measured by titration and can also be reported with the unit mg KOH/g.

The agents preferably include silicones in amounts of 0.01 wt. % to 15 wt. %, preferably 0.05 to 2 wt. %, based on total weight of the agent.

The composition can include, for example, at least one protein hydrolysate and/or one of its derivatives as a care substance of another compound class.

Protein hydrolysates are product mixtures obtained by acid-, base- or enzyme-catalyzed degradation of proteins (albumins). According to the invention, the term "protein hydrolysates" refers to total hydrolysates as well as individual amino acids and their derivatives as well as mixtures of different amino acids. The molecular weight of useful protein hydrolyzates ranges from 75, the molecular weight of glycine, to 200,000; preferably the molecular weight is 75 to 50,000 and more preferably 75 to 20,000 Dalton.

Protein hydrolysates that are added can be of vegetal as well as animal or marine or synthetic origin.

Animal protein hydrolyzates include elastin, collagen, keratin, silk protein, and milk albumin protein hydrolyzates, which can also be present in the form of their salts. Such products are marketed, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm) and Kerasol® (Croda).

The agents contain protein hydrolyzates, for example, in concentrations of 0.01 wt. % to 20 wt. %, preferably 0.05 wt. % to 15 wt. % and quite preferably in amounts of 0.05 wt. % to 5 wt. %, based on total end-use preparation.

Agents according to the invention can also contain at least one vitamin, one provitamin, one vitamin precursor and/or one of their derivatives as the care substance.

Preferred vitamins, provitamins and vitamin precursors which are normally classified in the groups A, B, C, E, F and H.

Retinol (vitamin $A_1$) as well as 3,4-didehydroretinol, (vitamin $A_2$) belong in the group of substances designated as vitamin A. β-carotene is the provitamin of retinol. Examples of suitable vitamin A components are vitamin A acid and its esters, vitamin A aldehyde and vitamin A alcohol as well as its esters such as the palmitate and acetate. The agents preferably contain vitamin A components in amounts of 0.05 to 1 wt. %, based on total application preparation.

The vitamin B group or vitamin B complex include inter alia vitamin $B_1$ (thiamine), vitamin $B_2$ (riboflavin), vitamin $B_3$ (nicotinic acid and/or nicotinic acid amide (niacinamide)), vitamin $B_5$ (pantothenic acid, panthenol and pantolactone), vitamin $B_6$ (pyridoxine as well as pyridoxamine and pyridoxal), vitamin C (ascorbic acid), vitamin E (tocopherols, especially α-tocopherol), vitamin F (linoleic acid and/or linolenic acid), vitamin H.

The agents preferably contain vitamins, provitamins and vitamin precursors from groups A, B, C, E and H. Panthenol, pantolactone, pyridoxine and its derivatives, as well as nicotinamide and biotin are especially preferred.

D-panthenol is preferably used as a care substance, optionally in combination with at least one of the abovementioned silicone derivatives.

Like the addition of glycerin and/or propylene glycol, the addition of panthenol increases the flexibility of the polymer film formed when the agent is used. Thus, if a particularly flexible hold is desired, then the agents can include panthenol instead of or in addition to glycerin and/or propylene glycol. In a preferred embodiment, the agents contain panthenol, preferably in an amount of 0.05 to 10 wt. %, more preferably 0.1 to 5 wt. %, based on total agent.

The agents can further include at least one plant extract as a care substance.

Usually, these extracts are manufactured by extraction of the whole plant. In individual cases, however, it can be preferred to produce the extracts solely from blossoms and/or leaves of the plant.

According to the invention, extracts mainly from green tea, oak bark, stinging nettle, hamamelis, hops, henna, chamomile, burdock root, field horsetail, hawthorn, linden flowers, almonds, aloe vera, spruce needles, horse chestnut, sandal wood, juniper, coconut, mango, apricot, lime, wheat, kiwi, melon, orange, grapefruit, sage, rosemary, birch, malva, lady's smock, common yarrow, thyme, lemon balm, restharrow, coltsfoot, marshmallow (althea), meristem, ginseng and ginger are preferred.

In addition, it can be preferred to use mixtures of a plurality, particularly two different plant extracts in the agents.

Mono- or oligosaccharides can also be incorporated as care substance into the agents.

Both monosaccharides as well as oligosaccharides, such as raw sugar, lactose and raffinose can be incorporated. According to the invention, use of monosaccharides is preferred. Monosaccharides preferably include those compounds having 5 or 6 carbon atoms.

Suitable pentoses and hexoses include ribose, arabinose, xylose, lyxose, allose, altrose, glucose, mannose, gulose, idose, galactose, talose, fucose and fructose. Arabinose, glucose, galactose and fructose are preferred incorporated carbohydrates; glucose is quite particularly preferably incorporated, and is suitable both in the D(+) or L(−) configuration or as the racemate. In addition, derivatives of these pentoses and hexoses can also be incorporated, such as the corresponding onic and uronic acids (sugar acids), sugar alcohols, and glycosides. Preferred sugar acids are gluconic acid, glucuronic acid, sugar acids, mannosugar acids and mucic acids. Preferred sugar alcohols are sorbitol, mannitol and dulcitol. Preferred glycosides are methyl glucosides. As the incorporated mono- and oligosaccharides are typically obtained from natural raw materials such as starch, they generally have configurations corresponding to these raw materials (e.g., D-glucose, D-fructose and D-galactose).

The agents preferably contain mono- or oligosaccharides in an amount of 0.1 to 8 wt. %, more preferably 1 to 5 wt. %, based on total end-use preparation.

The composition can further contain at least one lipid as a care substance.

According to the invention, suitable lipids are phospholipids such as soy lecithin, egg lecithin and cephalins, as well as the substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are commercialized, for example, by the Mona Company under the trade names Phospholipid EFA®, Phospholipid PIC® and Phospholipid SV®. The agents preferably contain lipids in amounts of 0.01 to 10 wt. %, particularly 0.1 to 5 wt. %, based on total end-use preparation.

Oil bodies are also suitable as a care substance.

Natural and synthetic cosmetic oil bodies include:

vegetal oils. Examples of such oils are sunflower oil, olive oil, soya oil, rapeseed oil, almond oil, jojoba oil, orange oil, wheat germ oil, peach stone oil and the liquid parts of coconut oil. However, other triglyceride oils such as the liquid fractions of beef tallow are also suitable as well as synthetic triglyceride oils, liquid paraffin oils, isoparaffin oils and synthetic hydrocarbons, as well as di-n-alkyl ethers containing a total of 12 to 36 carbon atoms, particularly 12 to 24 carbon atoms such as di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether and di-tert.butyl ether, diisopentyl ether, di-3-eth-yldecyl ether, tert.butyl n-octyl ether, isopentyl n-octyl ether and 2-methylpentyl n-octyl ether. The commercial products of the compounds 1,3-di-(2-ethylhexyl)cyclo-hexane (Cetiol® S) and di-n-octyl ether (Cetiol® OE) can be preferred.

Ester oils. Ester oils are the esters of $C_6$-$C_{30}$ fatty acids with $C_2$-$C_{30}$ fatty alcohols. Monoesters of fatty acids with alcohols containing 2 to 24 carbon atoms are preferred. According to the invention, isopropyl myristate (Rilanit® IPM), isononanoic acid $C_{16-18}$ alkyl ester (Cetiol® SN), 2-ethylhexyl palmitate (Cegesoft® 24), stearic acid 2-ethylhexyl ester (Cetiol® 868), cetyl ole-ate, glycerin tricaprylate, cocofatty alcohol caprinate/-caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol®B), myristyl myristate (Cetiol® MM), cetearyl isononanoate (Cetiol® SN), oleic acid decyl ester (Cetiol® V) are particularly preferred.

Dicarboxylic acid esters such as di-n-butyl adipate, di-(2-ethylhexyl) adipate, di-(2-ethylhexyl) succinate and di-isotridecyl acetate as well as diol esters such as ethylene glycol dioleate, ethylene glycol di-isotridecanoate, propylene glycol di(2-ethylhexanbate), propylene glycol di-isostearate, propylene glycol di-pelargonate, butane diol di-isostearate, neopentyl glycol dicaprylate, symmetrical, unsymmetrical or cyclic esters of carbon dioxide with fatty alcohols, as described in DE-OS 197 56 454, glycerin carbonate or dicaprylyl carbonate (Cetiol® CC), trifatty acid esters of saturated and/or unsaturated linear and/or branched fatty acids with glycerin, fatty acid partial glycerides, which include monoglycer-ides, diglycerides and their industrial mixtures. When using industrial products, minor amounts of triglycer-ides may still be contained as a result of the production process. The partial glycerides preferably comply with the Formula (D4-I),

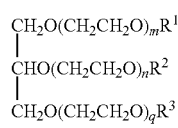

(D4-I)

wherein $R^1$, $R^2$ and $R^3$ are, independently of each other, hydrogen or a linear or branched, saturated and/or unsaturated acyl group containing 6 to 22 carbon atoms, preferably 12 to 18 carbon atoms, with the proviso that at least one of these groups is an acyl group and at least one of these groups is hydrogen. The sum of (m+n+q) is 0 or a number from 1 to 100, preferably 0 or 5 to 25. Preferably, $R^1$ is an acyl group, $R^2$ and $R^3$ are hydrogen, and the sum of (m+n+q) is 0. Typical examples are mono- and/or diglycerides based on caproic acid, caprylic acid, 2-eth-ylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Oleic acid monoglycerides are preferably employed.

The added amount of natural and synthetic cosmetic oil bodies in the agents is usually 0.1 to 30 wt. %, based on total end-use preparation, preferably 0.1 to 20 wt. %, and particularly 0.1 to 15 wt. %.

Although each of the cited care substances alone already provides a satisfactory result, according to the present invention all embodiments wherein the agent contains a plurality of conditioners, even from different groups, are included.

With the addition of a UV filter, both the agent and the treated fibers can be protected against damage from UV radiation. Consequently, at least one UV filter is preferably added to the agent. Suitable UV filters are generally not limited with respect to their structure and physical properties. Indeed, all UV filters that can be used in the cosmetic field having an absorption maximum in the UVA (315-400 nm), UVB (280-315 nm) or UVC (<280 nm) regions are suitable. UV filters having an absorption maximum in the UVB region, especially in the range from about 280 to about 300 nm, are particularly preferred.

Preferred UV-filters are chosen from substituted ben-zophenones, p-aminobenzoates, diphenylacrylates, cinnama-tes, salicylates, benzimidazoles and o-aminobenzoates.

Examples of usable UV-filters are 4-amino-benzoic acid, N,N,N-trimethyl-4-(2-oxoborn-3-ylidenemethyl)aniline methyl sulfate, 3,3,5-trimethylcyclohexyl salicylate (Homo-salate), 2-hydroxy-4-methoxy-benzophenone (Benzophe-none-3; Uvinul® M 40, Uvasorb® MET, Neo Heliopan® BB, Eusolex® 4360), 2-phenylbenzimidazol-5-sulfonic acid and their potassium, sodium and triethanolamine salts (phe-nylbenzimidazole sulfonic acid; Parsol® HS; Neo Helio-pan® Hydro), 3,3'-(1,4-phenylenedimethylene)-bis(7,7-dim-ethyl-2-oxo-bicyclo-[2.2.1]hept-1-yl-methanesulfonic acid) and their salts, 1-(4-tert.-butylphenyl)-3-(4-methoxyphenyl) propane-1,3-dione (butylmethoxydibenzoylmethane; Par-sol® 1789, Eusolex® 9020), a-(2-oxoborn-3-ylidene)-tolu-ene-4-sulfonic acid and salts thereof, ethoxylated ethyl 4-aminobenzoate (PEG-25 PABA; Uvinul® P 25), 2-ethyl-hexyl 4-dimethylaminobenzoate (Octyl Dimethyl PABA; Uvasorb® DMO, Escalol® 507, Eusolex® 6007), 2-ethyl-hexyl salicylate (Octyl Salicylate; Escalol® 587, Neo Helio-pan® OS, Uvinul® 018), isopentyl 4-methoxycinnamate (isoamyl p-methoxycinnamate; Neo Heliopan® E 1000), 2-ethylhexyl 4-methoxycinnamate (Octyl Methoxycin-namate; Parsol® MCX, Escalol® 557, Neo Heliopan® AV), 2-hydroxy-4-methoxybenzophenone-5-sulfonic acid and sodium salts thereof, (benzophenone-4; Uvinul® MS 40; Uvasorb® S 5), 3-(4'-methylbenzylidene)-D,L-camphor (4-methylbenzylidene camphor; Parsol® 5000, Eusolex® 6300), 3-benzylidene-camphor (3-Benzylidene camphor), 4-isopropylbenzyl salicylate, 2,4,6-trianilino-(p-carbo-2'-ethylhexyl-1'-oxy)-1,3,5-triazine, 3-imidazol-4-yl-acrylic acid and its ethyl ester, polymers of N-{(2 and 4)-[2-oxoborn-3-ylidenemethyl]benzyl}-acrylamide, 2,4-dihydroxyben-zophenone (Benzophenone-1; Uvasorb® 20 H, Uvinul® 400), 2-ethylhexyl ester of 1,1'-diphenylacrylonitrilic acid (Octocrylene; Eusolex® OCR, Neo Heliopan® Type 303, Uvinul® N 539 SG), menthyl o-aminobenzoate (menthyl anthranilate; Neo Heliopan® MA), 2,2',4,4'-tetrahydroxy-benzophenone (Benzophenone-2, Uvinul® D-50), 2,2'-dihy-droxy-4,4'-dimethoxybenzophenone (Benzophenone-6), sodium 2,2'-dihydroxy-4,4'-dimethoxybenzophenone-5-sul-fonate and 2'-ethylhexyl 2-cyano-3,3-diphenylacrylate.

2-Hydroxy-4-methoxy-benzophenone-5-sulfonic acid and its sodium salt and/or ethoxylated ethyl 4-aminobenzoate are preferred.

The agent usually contain UV filters in amounts of 0.01 to 5 wt. %, based on total end-use preparation. Quantities of 0.1-2.5 wt. % are preferred.

In a particular embodiment, the agent further contains one or more substantive dyes. Application of the agent enables the treated keratinic fiber not only to be temporarily styled, but also dyed at the same time. This can be particularly desirable when only a temporary dyeing is desired, for example, with flamboyant fashion colors that can be subsequently removed from the keratinic fibers by simply washing them out.

Substantive dyes include nitrophenylenediamines, nitroamino phenols, azo dyes, anthraquinones or indophenols. Preferred substantive dyestuffs are compounds with the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, Disperse Blue 12, Acid Blue 3, Acid Green 7, Acid Green 50, HC Violet 1, Disperse Violet 1, Disperse Violet 4, Acid Violet 43, Disperse Black 9, Acid Black 1, and Acid Black 52 known compounds as well as 1,4-diamino-2-nitrobenzene, 2-amino-4-nitrophenol, hydroxyethyl)-amino-2-nitrobenzene, 3-nitro-4-($\beta$-hydroxyethyl)-amino phenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)-amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-1-hydroxy-4-nitrobenzene. Cationic substantive dyes are preferably used. Particular preference is given here to—

(a) cationic triphenylmethane dyes, such as Basic Blue 7, Basic Blue 26, Basic Violet 2 and Basic Violet 14,
(b) aromatic systems substituted by a quaternary nitrogen group, such as Basic Yellow 57, Basic Red 76, Basic Blue 99, Basic Brown 16 and Basic Brown 17, and
(c) substantive dyes having a heterocycle that has at least one quaternary nitrogen atom, as specified, for example, in EP-A2-998 908 in claims 6 to 11.

Dyes also known under the names Basic Yellow 87, Basic Orange 31 and Basic Red 51, are particularly preferred cationic substantive dyes of group (c). Cationic substantive dyes commercialized under the trade name Arianor® are likewise quite preferred cationic substantive dyes according to the invention.

The agents according to this embodiment contain substantive dyes preferably in an amount of 0.001 to 20 wt. %, based on total agent.

Preferably, the agents are exempt from oxidation dye precursors. Oxidation dye precursors are divided into developer components and coupler components. Under the influence of oxidizing agents or from atmospheric oxygen, the developer components form the actual colorants among each other or by coupling with one or more coupler components.

Formulation of the agents can be in all forms typical for styling agents, such as solutions that can be applied as hair water or pump or aerosol spray onto the hair, in the form of creams, emulsions, waxes, gels, or also surfactant-containing foaming solutions or other preparations suitable for application on the hair.

Hair creams and gels generally contain structurants and/or thickening polymers which give the desired consistency to the products. Structurants and/or thickening polymers are typically added in amounts of 0.1 to 10 wt. %, based on total product. Quantities of 0.5 to 5 wt. %, particularly 0.5 to 3 wt. %, are preferred.

The agents are preferably packaged as a pump spray, aerosol spray, pump foam or aerosol foam.

The agents can be packed in a dispensing device, illustrated by either a pressurized gas container additionally containing a propellant ("aerosol container") or by a non-aerosol container.

Pressurized gas containers, wherein a product is dispersed through a valve by the internal gas pressure in the container, are defined as "aerosol containers". The opposite of aerosol, a container under normal pressure, is a "non-aerosol container", from which a product is dispersed by mechanical actuation of a pump system.

Agents according to the invention are preferably packed as an aerosol hair foam or aerosol hair spray. Consequently, the agent additionally contains at least one propellant.

Suitable propellants include $N_2O$, dimethyl ether, $CO_2$, air, alkanes containing 3 to 5 carbon atoms such as propane, n-butane, iso-butane, n-pentane and iso-pentane, and their mixtures. Dimethyl ether, propane, n-butane, iso-butane and their mixtures are preferred.

According to a preferred embodiment, the alkanes, mixtures of the alkanes, or mixtures of the alkanes with dimethyl ether are preferred as the sole propellant. However, the invention also includes joint use with fluorochlorohydrocarbon propellants, especially fluorinated hydrocarbons.

Regarding the weight ratio of propellant to typical ingredients of the preparation, the size of the aerosol droplets or foam bubbles and the relevant size distribution can be adjusted for a given spray device.

The amount of added propellant varies as a function of actual composition of the agent, packaging used, and the desired product type, for example, hair spray or hair foam. When a conventional spray device is used, aerosol foam products preferably include propellant in amounts of 1 to 35 wt. %, based on total product. Quantities of 2 to 30 wt. %, especially 3 to 15 wt. %, are particularly preferred. Aerosol sprays generally contain greater amounts of propellant. For aerosol sprays, the propellant is preferably added in amounts of 30 to 98 wt. %, based on the product. Quantities of 40 to 95 wt. %, especially 50 to 95 wt. %, are particularly preferred.

Aerosol products can be manufactured using conventional techniques. Generally, all ingredients of the agent except propellant are charged into a suitable pressure-resistant container. This is then sealed with a valve. The desired amount of propellant is then filled by conventional techniques.

Agents in the form of gels are foamed in a two-chamber aerosol container, preferably with isopentane as the propellant, which is incorporated into the agent and packed in the first chamber of the two-chamber aerosol container. At least one additional propellant different from isopentane is packed in the second chamber of the two-chamber aerosol container and generates a higher pressure than the isopentane. The propellants of the second chamber are preferably chosen from $N_2O$, dimethyl ether, $CO_2$, air, alkanes containing 3 or 4 carbon atoms (such as propane, n-butane, iso-butane), as well as mixtures thereof.

Aerosol hair foams or aerosol hair sprays containing the above described agent and at least one propellant are a preferred embodiment of the agent.

Preferred agents and propellants of aerosol hair foam or aerosol hair spray, as well as relevant amounts of propellant correspond to those already mentioned above.

A second subject matter of the invention is use of agents according to the invention for temporary shaping of hair and/or for hair care.

The agents and products containing these agents, especially aerosol hair foams or aerosol hair sprays, give treated hair a very strong, long-lasting hold to the hairstyle, while the hair remains flexible. If the agent is hair foam, then a stable, micro-porous and creamy foam is formed that can be uniformly dispersed on the hair without dripping.

A third subject matter of the invention is a method for treating keratin-containing fibers, especially human hair, wherein an agent according to the first subject matter is foamed to a foam by a dispensing device, and the resulting foam is applied onto the keratin-containing fibers.

Preferably, the keratin-containing fibers are shaped and this shape is fixed by the agent of the first subject matter of the invention.

The abovementioned dispensing devices are preferred.

A fourth subject matter of the invention is a method for treating keratin-containing fibers, especially human hair, wherein an agent according to the first subject matter is applied as a spray onto the keratin-containing fibers by a dispensing device.

Preferably, the keratin-containing fibers are shaped and this shape is fixed by the agent of the first subject matter of the invention.

The abovementioned dispensing devices are preferred.

The following examples are intended to illustrate the subject matter of the present invention in more detail, without limiting it in any way.

EXAMPLES

Unless otherwise stated, the quantities are in weight percent.

The following formulations were prepared by blending the listed raw materials:

| Raw Material | A | B | C | D |
|---|---|---|---|---|
| Amphomer[1] | 2.0 | — | 3.0 | 4.0 |
| 2-Amino-2-methylpropan-1-ol | 0.4 | 0.2 | 0.5 | 0.7 |
| Aquastyle ® 300 | 3.0 | 2.0 | 4.0 | 3.5 |
| Luvimer ® 36D[2] | — | 1.0 | — | — |
| PEG-40 hydrogenated castor oil | 0.1 | 0.2 | 0.2 | 0.1 |
| Water | | ad 100 | | |

[1](100% active substance) INCI name: Octylacrylamide/Acrylates/Butylaminoethylmethacrylate Copolymer) (National Starch)
[2]Copolymer of tert-butyl acrylate, ethyl acrylate, methacrylic acid (36 wt. % active substance in water; INCI name: Acrylates Copolymer) (BASF SE)

All formulations were free of turbidity.

All formulations when applied onto the hair produced an outstandingly flexible hold to the hairstyle. The hair received a very good care.

We claim:

1. Agent for treating keratin-containing fibers comprising in a cosmetically acceptable carrier:
   a) at least one amphiphilic, cationic polymer having at least one structural unit of Formula (I), at least one structural unit of Formula (II), at least one structural unit of Formula (III), and at least one structural unit of Formula (IV),

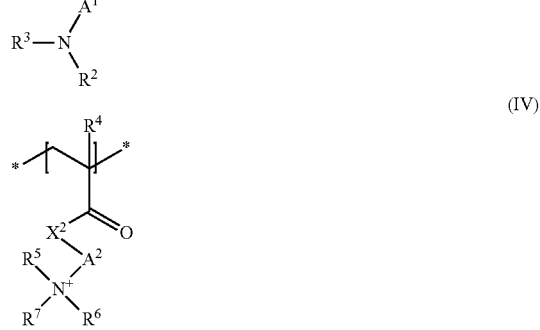

wherein $R^1$ and $R^4$ are, independently of one another, a hydrogen atom or a methyl group, $X^1$ and $X^2$ are, independently of one another, an oxygen atom or an NH group, $A^1$ and $A^2$ are, independently of one another, an ethane-1,2-diyl, propane-1,3-diyl or butane-1,4-diyl group, $R^2$, $R^3$, $R^5$ and $R^6$ are, independently of one another, a ($C_1$ to $C_4$) alkyl group, $R^7$ is a ($C_8$ to $C_{30}$) alkyl group, and b) 0.1 wt % to 20.0 wt. %, based on total weight of the agent of at least one film-forming anionic and/or setting anionic polymer having at least one structural unit of Formula (V) and at least one structural unit of Formula (VI),

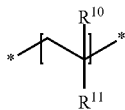
(VI)

wherein $R^8$ and $R^9$ are, independently of one another, a hydrogen atom or a methyl group, with the proviso that $R^8$ and $R^9$ are not simultaneously methyl, $R^{10}$ is a hydrogen atom or a methyl group, $R^{11}$ is a carbamoyl group, a linear or branched ($C_4$ to $C_{12}$) alkylaminocarbonyl group, a linear or branched ($C_4$ to $C_{12}$) alkylaminoethyl-aminocarbonyl group, a linear or branched ($C_4$ to $C_{12}$) alkylaminopropyl-aminocarbonyl group, a linear or branched ($C_4$ to $C_{12}$) alkyloxycarbonyl group, a linear or branched ($C_4$ to $C_{12}$) alkylaminoethyloxycarbonyl group, a linear or branched ($C_4$ to $C_{12}$) alkylaminopropyloxycarbonyl group, a linear or branched ($C_2$ to $C_{12}$) acyloxy group, $A^3$ is a hydroxyl group or an organic group having at least one sulfonic acid group that bonds through an oxygen atom or an NH group to the structural fragment.

2. Agent according to claim 1 wherein $R^1$ and $R^4$ are each a methyl group.

3. Agent according to claim 1 wherein $A^1$ and $A^2$ are, independently of one another, ethane-1,2-diyl or propane-1,3-diyl.

4. Agent according to claim 1 wherein $R^2$, $R^3$, $R^5$ and $R^6$ are, independently of one another, methyl or ethyl.

5. Agent according to claim 1 wherein $R^7$ is a ($C_{10}$ to $C_{24}$) alkyl group.

6. Agent according to claim 1 wherein $R^7$ is decyl (caprinyl), dodecyl (lauryl), tetradecyl (myristyl), hexadecyl (cetyl), octadecyl (stearyl), eicosyl (arachyl) or docosyl (behenyl).

7. Agent according to claim 1 wherein the at least one amphiphilic, cationic polymer comprises at least one structural unit of Formula (II), at least one structural unit of Formula (III-8), and at least one structural unit of Formula (IV-8)

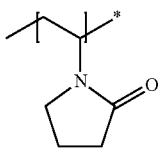
(I)

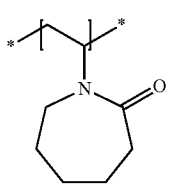
(II)

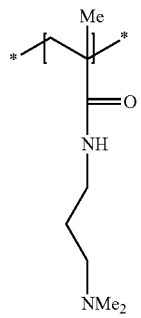
(III-8)

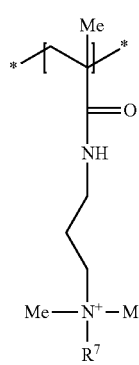
(IV-8)

wherein $R^7$ is octyl (capryl), decyl (caprinyl), dodecyl (lauryl), tetradecyl (myristyl), hexadecyl (cetyl), octadecyl (stearyl), eicosyl (arachyl) or docosyl (behenyl).

8. Agent according to claim 1 wherein the at least one amphiphilic, cationic polymer is present in an amount of 0.1 wt. % to 20.0 wt. %, based on total weight of the agent.

9. Agent according to claim 1 wherein the film-forming anionic and/or setting anionic polymer (b) comprises at least one structural unit of Formula (V) chosen from at least one structural unit of Formulae (V-1) to (V-5)

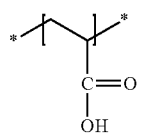
(V-1)

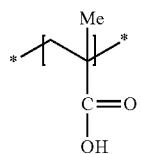
(V-2)

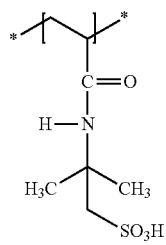
(V-3)

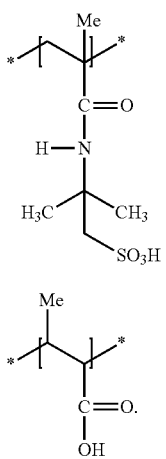 (V-4)
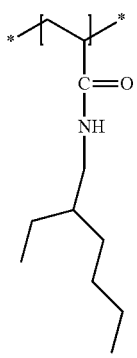 (V-5)
10. Agent according to claim 1 wherein the film-forming anionic and/or setting anionic polymer (b) comprises at least one structural unit of Formula (VI) chosen from at least one structural unit of Formulae (VI-1) to (VI-15)
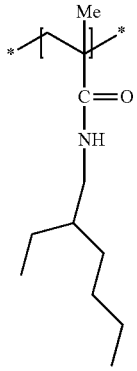 (VI-1)
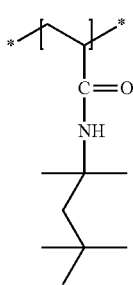 (VI-2)
(VI-3)
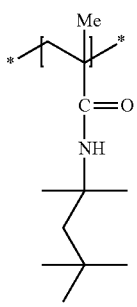 (VI-4)
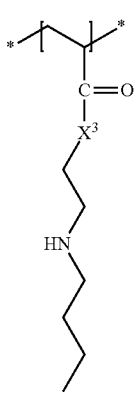 (VI-5)
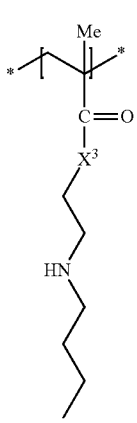 (VI-6)
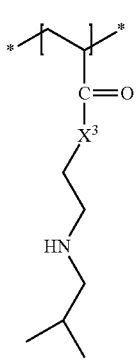 (VI-7)

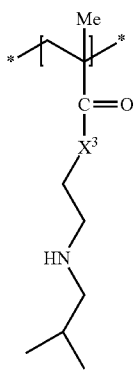

(V-8)

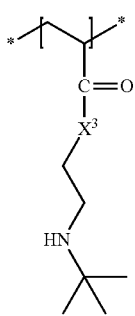

(V-9)

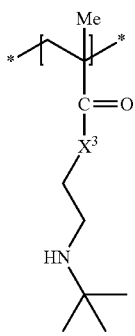

(VI-10)

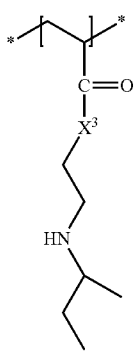

(VI-11)

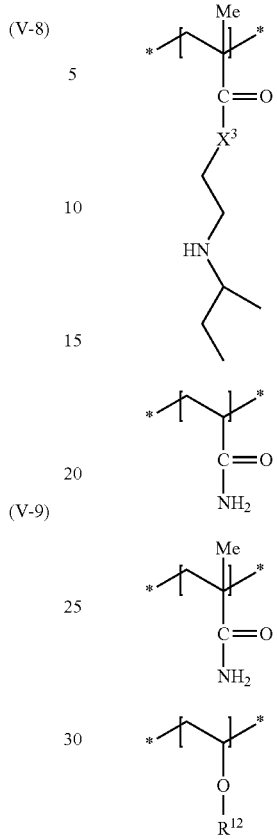

(VI-12)

(VI-13)

(VI-14)

(VI-15)

wherein
$X^3$ is an oxygen atom or an NH group, and
$R^{12}$ is a ($C_2$ to $C_{12}$) acyl group.

11. Agent according to claim 1 wherein the film-forming anionic and/or setting anionic polymer (b) is chosen from at least one of the following polymers:

copolymers of acrylic acid, ($C_1$ to $C_4$) alkyl acrylates, $C_4$ alkylaminoethyl methacrylate and $C_8$ alkyl acrylamide, copolymers of 2-acrylamido-2-methyl-propane sulfonic acid and acrylamide, copolymers of 2-acrylamido-2-methyl-propane sulfonic acid, acrylamide and acrylic acid, copolymers of vinyl acetate and crotonic acid, copolymers of vinyl propionate and crotonic add, copolymers of vinyl neodecanoate, vinyl acetate and crotonic acid, or copolymers of methacrylic acid and ethyl acrylate and tert-butyl acrylate.

12. Aerosol foam or spray comprising the agent according to claim 1.

13. Method for treating keratin-containing fibers comprising foaming an agent according to claim 1 to a foam by a dispensing device, and applying the resulting foam onto the keratin-containing fibers.

14. Method for treating keratin-containing fibers comprising applying an agent according claim 1 as a spray onto the keratin-containing fibers by a dispensing device.

15. Agent for treating keratin-containing fibers comprising in a cosmetically acceptable carrier:

a) at least one amphiphilic, cationic polymer comprising polyquaternium-69, wherein the amphiphilic, cationic polymer is present in an amount of 0.5 wt. % to 5.0 wt. % based on total weight of the agent; and b) at least one film-forming anionic and/or setting anionic polymer having at least one structural unit of Formula (V) and at least one structural unit of Formula (VI):

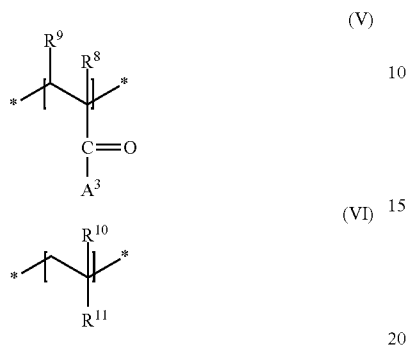

wherein:

$R^8$ is a methyl group, $R^9$ is a hydrogen atom, $R^{10}$ is a hydrogen atom, $R^{11}$ is a linear or branched ($C_4$ to $C_{12}$) alkyloxycarbonyl group, and $A^3$ is a hydroxyl group, and wherein the film-forming anionic and/or setting anionic polymer is present in an amount of 0.5 wt. % to 10 wt. % based on total weight of the agent.

* * * * *